United States Patent [19]

Metzger

[11] 4,006,222
[45] Feb. 1, 1977

[54] PURIFICATION OF NYSTATIN

[75] Inventor: Julio Metzger, East Brunswick, N.J.

[73] Assignee: E. R. Squibb & Sons, Inc., Princeton, N.J.

[22] Filed: Oct. 20, 1975

[21] Appl. No.: 623,840

[52] U.S. Cl. ............................................. 424/123
[51] Int. Cl.$^2$ ...................................... A61K 35/00
[58] Field of Search .................................. 424/123

[56] References Cited

UNITED STATES PATENTS

| | | | |
|---|---|---|---|
| 2,865,807 | 12/1958 | Dutcher et al. | 424/123 |
| 3,332,844 | 7/1967 | Vandeputte et al. | 424/123 |
| 3,517,100 | 6/1970 | Renella | 424/123 |
| 3,517,101 | 6/1970 | Esse | 424/123 |

*Primary Examiner*—Albert T. Meyers
*Assistant Examiner*—Daren M. Stephens
*Attorney, Agent, or Firm*—Lawrence S. Levinson; Merle J. Smith; Donald J. Barrack

[57] ABSTRACT

Crude, partially purified, or contaminated nystatin is purified by suspending the nystatin starting material in a lower alkanol, treating the suspension with an organic acid, filtering the suspension to remove residual solids, adding a chlorinated hydrocarbon solvent to the alkanol filtrate, neutralizing the mixture, and precipitating the nystatin by the addition of water.

7 Claims, No Drawings

PURIFICATION OF NYSTATIN

BACKGROUND OF THE INVENTION

The present invention relates to the antibiotic nystatin (referred to in the older literature as fungicidin), and more specifically to a process for the purification of crude, partially purified or contaminated nystatin.

Nystatin and its method of preparation from *Streptomyces noursei* are disclosed by Hazen et al. in U.S. Pat. No. 2,797,183. Reference may also be made to Hazen and Brown, "Fungicidin, An Antibiotic Produced by a Soil Actinomycete," Proc. Soc. Exptl. Biol. Med. 76:93 (1950) and Brown, Hazen and Mason, "Effect of Fungicidin (nystatin) in Mice Injected with Lethal Mixtures of Aureomycin and *Candida albicans*," Science 117:609 (1953). The antibiotic is hereinafter referred to by the single term "nystatin".

Several methods for isolating nystatin from the fermentation media are known to the prior art. Examples of such processes are Hazen et al., U.S. Pat. No. 2,797,183; Vandeputte et al., U.S. Pat. No. 2,786,781; Vandeputte et al., U.S. Pat. No. 3,332,844; and Renella, U.S. Pat. No. 3,517,100. The nystatin isolated by known processes is not a highly purified, uniformly crystalline product. A method for obtaining nystatin in such a form is of course highly desirable, and several methods for achieving this result have been suggested by the prior art, but each has certain drawbacks. For examples of such processes, reference may be made to Vandeputte, U.S. Pat. No. 2,832,719; Dutcher et al., U.S. Pat. No. 2,865,807; Mendelsohn, U.S. Pat. No. 3,509,255; and Esse, U.S. Pat. No. 3,517,101.

BRIEF SUMMARY OF THE INVENTION

It is an object of this invention to provide a process for the purification of crude, partially purified, or contaminated nystatin.

It is an object of this invention to provide a process for the purification of nystatin that will yield a product of high potency.

It is an object of this invention to provide a process for the purification of nystatin that minimizes the danger of inactivation of nystatin due to accidental over dosage of acid.

It is an object of this invention to provide a highly purified nystatin product which can be readily converted into a highly crystalline form.

It is an object of this invention to provide a process for the purification of nystatin that can be easily controlled on a production scale.

It is an object of this invention to provide a process for the purification of nystatin that utilizes conventional equipment and commercially available reagents and solvents.

These, and other objects that will be readily apparent from the description of the invention, are realized by the process of this invention. The process comprises:

i. suspending crude, partially purified, or contaminated nystatin in a lower alkanol;
ii. solubilizing the nystatin with a weak organic acid;
iii. filtering off the lower alkanol extract;
iv. adding a chlorinated hydrocarbon solvent to the lower alkanol extract;
v. neutralizing the mixture of chlorinated hydrocarbon solvent and lower alkanol extract; and
vi. precipitating the purified nystatin by the addition of water.

DETAILED DESCRIPTION OF THE INVENTION

The nystatin employed as the starting material in the novel purification process of this invention can be crude, partially purified, or contaminated nystatin. The expression "contaminated nystatin" encompasses not only nystatin that contains chemical contaminants, but also nystatin contaminated with physical contaminants such as dirt particles, fibrous material, and other particulate elements that might cause nystatin to be unacceptable for pharmaceutical utility.

The first step of the process of this invention is the suspending of the nystatin starting material in a lower alkanol, i.e., an alkanol having 1, 2, 3, or 4 carbon atoms; methanol is preferred. The amount of lower alkanol used is not critical, but the activity of the nystatin in suspension should be at least about 25,000 units/milliliter, preferably at least about 100,000 units/milliliter.

After suspending the nystatin in the lower alkanol, a weak organic acid is added. By a weak organic acid is meant an acid which belongs to the category of mono- or polybasic organic acids, which also may contain one or more hydroxyl groups, with a $pK_a$ at 25° C of 1.0 to 5.0. Exemplary organic acids are acetic, maleic and citric acids; acetic and citric acids are preferred, and citric acid is the most preferred. The amount of acid added to the suspension will of course vary with the particular acid, but will be sufficient to solubilize the nystatin.

The lower alkanol extract is filtered off. To improve the efficiency of the filtration process, a filter aid, such as diatomaceous silica, may be added to the suspension. Activated carbon may also be added, but is not required.

In a preferred embodiment of this invention, the spent cake is washed with portions of fresh lower alkanol to insure a more complete recovery of the nystatin. The lower alkanol washes should be added to the lower alkanol extract prior to proceeding with the process.

A chlorinated hydrocarbon solvent is added to the lower alkanol extract. Exemplary solvents are chloroform, dichloromethane, and others. For reasons of safety, dichloromethane is the preferred solvent. The chlorinated hydrocarbon solvent is added to the lower alkanol extract in an amount of from about 0.1 to 5.0 milliliters per million units of activity.

The mixture of solvent and lower alkanol extract is neutralized to a pH of about 6.0 to 8.0 with a suitable base. Exemplary bases are triethanolamine, diethylamine, triethylamine, ammonia, and sodium hydroxide.

The purified nystatin is precipitated by the addition of water to the mixture and recovered using conventional procedures. A preferred procedure is the addition of nystatin seed crystals followed by heating at reflux, followed by cooling to below room temperture, preferably to about 0° to 15° C. The resulting crystalline nystatin is separated, e.g., by filtration or centrifugation.

The following examples are illustrative of the invention.

EXAMPLE 1

Salvage nystatin (15.4g, microbiological potency 4490 units/milligram) is slurried in 300ml of methanol at a temperature of about 16° C. Citric acid monohydrate (7.5g) is added to the slurry and the slurry is agitated for 30 minutes to give a hazy solution. Diatomaceous silica (2.0g) is added and the slurry is vacuum filtered to remove residual solids. The residue is displacement washed with three 25ml portions of methanol and the washes are added to the methanol filtrate. The methanol filtrate is agitated and 75ml of dichloromethane, 30ml of 40% triethanolamine-water, and 560ml of cold, distilled water are added in sequence over a 5-minute period to give a slurry of amorphous nystatin. An additional 6ml of 40% triethanolamine-water is added to the slurry to adjust the pH to about 6.6 to 7.0, and 375mg of nystatin seed crystals are added. The slurry is warmed to reflux (41° C) in 15 minutes, gradually cooled to 10° C over a 2-hour period and maintained at this temperature for an additional hour.

The slurry of crystals is vacuum filtered and the crystals are displacement washed with 60ml of cold 40% methanol-water followed by three 75ml portions of acetone. The crystals are then vacuum dried for 20 hours at 45° C to give 10.72 grams of nystatin, microbiological potency 5360 units/milligram.

EXAMPLE 2

Crude nystatin (17.65g, microbiological potency 2940 units/milligram) is slurried in 200ml of methanol at a temperature of about 16° C. Citric acid monohydrate (7.5g) is added and the mixture is agitated for 30 minutes to give a suspension. Diatomaceous silica (1.0g) is added to the suspension which is then vacuum filtered to remove residual solids. The residue is displacement washed with three 17ml portions of methanol and the washes are added to the methanol filtrate. The methanol filtrate is agitated and 50ml of dichloromethane, 30ml of 40% triethanolamine-water and 350ml of cold, distilled water are added in sequence over a 5-minute period to give a slurry of amorphous nystatin. An additional 3.6ml of 40% triethanolamine-water is added to the slurry to adjust the pH to about 6.7 to 7.0. Nystatin seed crystals (500mg) are added, and the slurry is warmed to reflux (40° C) over a period of 14 minutes, gradually cooled to 10° C over a 2-hour period, and maintained at this temperature for an additional hour.

The slurry of crystals is vacuum filtered and the crystals are displacement washed with 40ml of cold 40% methanol-water followed by three 50ml portions of acetone. The crystals are then vacuum dried for 20 hours at 45° C to yield 7.12g of nystatin, microbiological potency 6000 units/milligram.

What is claimed is:
1. A process for the purification of nystatin which comprises:
   i. suspending nystatin in a lower alkanol;
   ii. solubilizing the nystatin with a weak organic acid having a $pK_a$ at 25° C of 1.0 to 5.0;
   iii. filtering off the lower alkanol extract;
   iv. combining a chlorinated hydrocarbon solvent with the lower alkanol extract;
   v. neutralizing the mixture of chlorinated hydrocarbon solvent and lower alkanol extract; and
   vi. adding water to precipitate purified nystatin.
2. A process in accordance with claim 1 which additionally comprises washing the spent filter cake obtained in step (iii) with a lower alkanol, and adding the lower alkanol washes to the lower alkanol extract.
3. A process in accordance with claim 1 which additionally comprises converting the precipitated nystatin to a crystalline form.
4. A process in accordance with claim 1 wherein the lower alkanol is methanol.
5. A process in accordance with claim 1 wherein the organic acid is citric acid.
6. A process in accordance with claim 1 wherein the chlorinated hydrocarbon solvent is dichloromethane.
7. A process in accordance with claim 1 which comprises:
   i. suspending nystatin in methanol;
   ii. solubilizing the nystatin with citric acid;
   iii. filtering off the methanol extract;
   iv. washing the resultant spent filter cake with methanol and adding the methanol washes to the methanol extract;
   v. combining dichloromethane with the methanol extract;
   vi. neutralizing the mixture of dichloromethane and methanol extract; and
   vii. adding water to the mixture to precipitate nystatin.

* * * * *